United States Patent [19]
Wheeler et al.

[11] Patent Number: 5,365,058
[45] Date of Patent: Nov. 15, 1994

[54] COMPENSATING OPTICAL SYSTEM FOR VIDEO MONITOR

[75] Inventors: Robert Wheeler, Skaneateles; Richard A. Tamburrino, Auburn; Robert J. Wood, Syracuse, all of N.Y.

[73] Assignee: Welch Allyn, Inc., Skaneateles Falls, N.Y.

[21] Appl. No.: 78,147

[22] Filed: Jun. 16, 1993

[51] Int. Cl.⁵ .................................................. H01J 3/14
[52] U.S. Cl. ..................................... 250/216; 348/72
[58] Field of Search ................... 250/216, 208.1, 560; 348/65, 72, 74, 75, 369, 76; 128/6

[56] References Cited

U.S. PATENT DOCUMENTS 4,884,133 11/1989 Kanno et al. ............................ 348/72
5,166,787 11/1992 Irion .......................................... 348/75

Primary Examiner—David C. Nelms
Assistant Examiner—K. Shami
Attorney, Agent, or Firm—Harris Beach & Wilcox

[57] ABSTRACT

There is disclosed a video system having a photodetector for sensing an optical pattern that is representative of a field of interest. The system incorporates a CCD photosensor having a pixel format adapted to a particular video convention, and further includes video electronics, a video output device such as a display, tape, or computer, which is adapted to a second video convention. The video output device introduces a distortion into the system in accordance with an incompatibility between the first video convention and the second video convention. To correct the distortion a cylindrical lens is disposed in the optical path extending from the photodetector to the field of interest, for varying at least one dimension of the optical pattern.

13 Claims, 4 Drawing Sheets

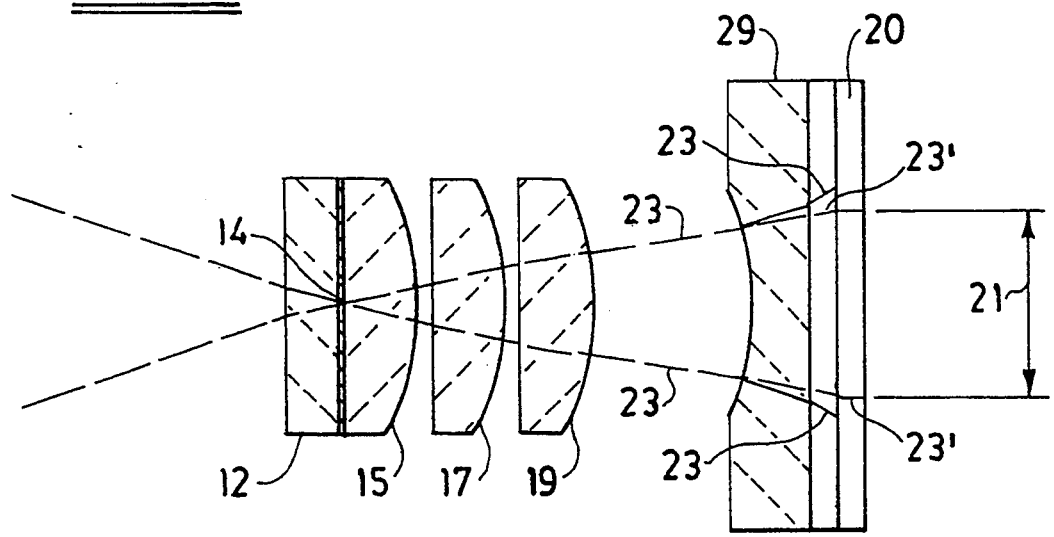
FIG. 2
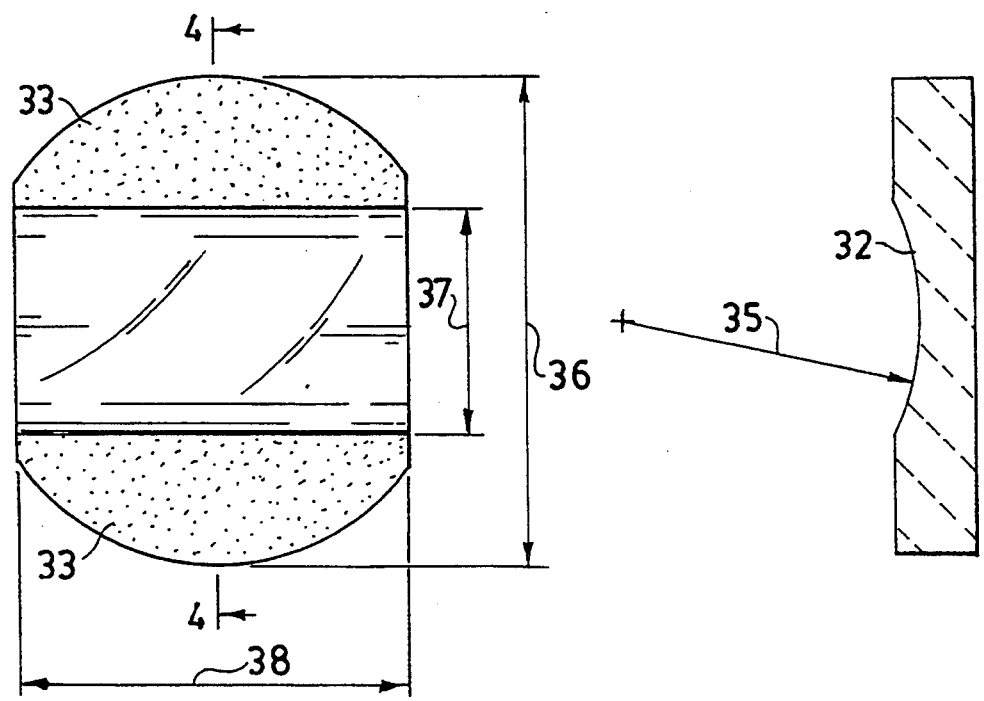
FIG. 3
FIG. 4

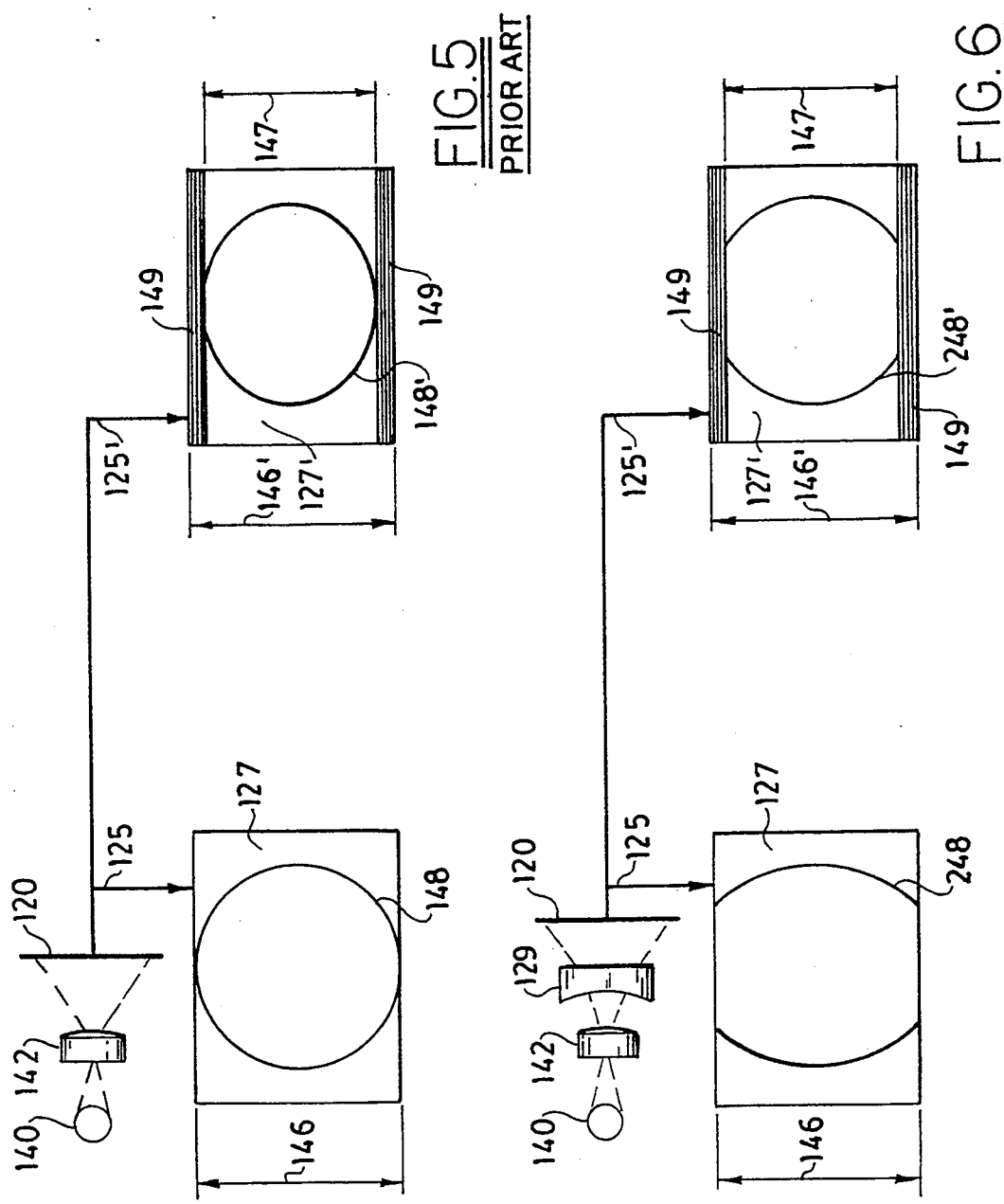

COMPENSATING OPTICAL SYSTEM FOR VIDEO MONITOR

BACKGROUND OF THE INVENTION

1. Field of the Invention

This invention relates to optical apparatus for correcting optical distortion in an imaging system. More particularly this invention relates to an imaging system wherein an optical assembly compensates for geometric incompatibility between the formatted output of a video sensor and a line monitor.

2. Description of the Prior Art

In endoscopic and related video systems it is common practice to employ single chip charge coupled devices (CCD) for image acquisition. The predominant video convention in the United States has long been NTSC, employing 525 scan lines, and it is the usual manufacturing practice to construct the CCD in a specific pixel format, for example 510 pixels per horizontal line and 488 horizontal lines. The format varies widely. 480 horizontal lines are known, as are formats employing 768 pixels per horizontal line. When the output of such a CCD device is coupled to suitable video processing electronics, the resulting composite signal accommodates the NTSC monitor screen. In other parts of the world different video conventions are employed, for example, the European PAL convention having an identical aspect ratio, but having 625 scan lines. Accommodating a 625 line PAL monitor would ideally require a CCD device having about 588 horizontal lines. A need exists in the art for utilizing existing single chip NTSC compatible CCDs with PAL and other non-NTSC monitors to avoid the expense of redesigning the CCD chip. As used herein, the terms "NTSC" AND "PAL" refer to the U.S. 525 line and the European 625 line color systems respectively, rather to the color modulation standards alone.

SUMMARY OF THE INVENTION

It is therefore a primary object of the present invention to provide apparatus that allows the use of a solid state CCD imager with a monitor having an incompatible video convention.

It is another object of the present invention to economically employ a solid state CCD imager for use with a specified line monitor without resort to retooling the CCD chip or modifying the video electronics.

It is yet another object of the present invention to use an existing 525 line compatible solid state CCD imager with a 625 line monitor.

These and other objects are attained by a video system having a photodetector for sensing an optical pattern that is representative of a field of interest, and formatted to a first video convention, for example NTSC. Video electronics are coupled to the photodetector, and reformats the synchronization and other functions to produce a video signal in accordance with a second video convention, such as PAL. A video output device, such as a display, tape, or computer, which is adapted to the second video convention, is connected to the video electronics. The image produced on the video output device has a systematic distortion however which is a consequence of an incompatibility between the first video convention and the second video convention. To correct the distortion a compensating lens is disposed in the optical path extending from the photodetector to the field of interest, for varying at least one dimension of the optical pattern.

In accordance with one aspect of the invention the compensating lens is a cylindrical lens having a horizontal axis and a concave face directed toward the field of interest for magnifying the vertical dimension of the optical pattern.

In accordance with another aspect of the invention the cylindrical lens has a vertical axis and a convex face directed toward the field of interest for minifying a horizontal dimension of said optical pattern.

In accordance with a further aspect of the invention the photodetector is a 525 line formatted CCD. The CCD and the compensating lens are incorporated into the distal end of an insertion tube of a video endoscope.

BRIEF DESCRIPTION OF THE DRAWINGS

For a better understanding of these and other objects of the present invention, reference is made to the detailed description of the invention which is to be read in conjunction with the following drawings, wherein:

FIG. 2 is a side elevation of an optical assembly suitable for use in the embodiment of FIG. 1 with detail omitted;

FIG. 3 is a plan view of a cylindrical compensating lens of FIG. 1;

FIG. 4 is a sectional view through line 4—4 of FIG. 3;

FIGS. 5 and 6 are diagrams which are helpful in understanding the operation of the invention.

DESCRIPTION OF THE PREFERRED EMBODIMENT

While the preferred embodiment is described with reference to a borescope, and to the 525 line and 625 line video conventions, the invention can be practiced in conjunction with endoscopes, other video probes, and virtually any video system employing an imager having a pixel format which is geometrically mismatched to the video convention employed by a screen display or other peripheral device that can be connected to the system's video electronics, such as a memory, tape, computer, or the like. For example the invention could be practiced with the 625 line SECAM system widely employed in France and the former Soviet Union.

Figure 1:
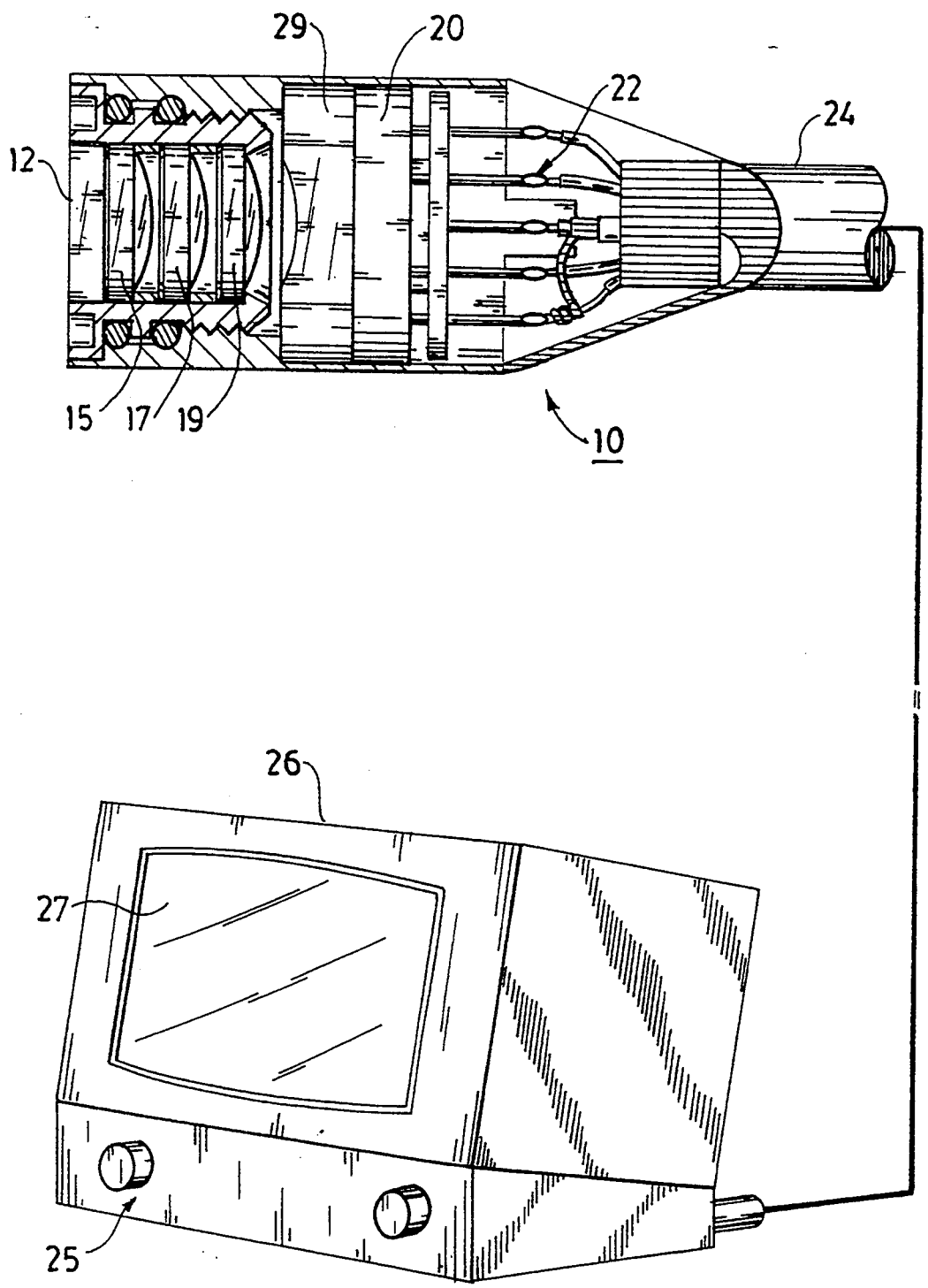
FIG. 1 is a partially diagrammatic sectional view of the distal end of a borescope or endoscope incorporating a video system in accordance with the invention.

Turning now to the drawings, there is shown in FIGS. 1 and 2 an optical assembly in accordance with the invention which has been incorporated into the distal end of a borescope or endoscope 10 which views a field of interest through an objective window 12. The optics, seen best in FIG. 2, include a small aperture 14, followed by a system of objective lenses 15, 17, 19. The objective lenses and aperture are designed and constructed in accordance with well known techniques to achieve a desired magnification and depth of field and to project an image onto an imager 20, preferably a 525 line formatted charge coupled device (CCD) with 510 pixels per horizontal line and 488 horizontal lines. Imager 20 has wire connections 22 to a cable or electrical harness 24, which leads through the borescope insertion tube to suitable video electronics 25. The electronics are coupled to a monitor 26 having a screen display 27 in order to enable the user to evaluate the field of view. The cable conducts power and other required signals to the imager as well as transmitting the signal output.

To understand the benefits of the invention it is helpful to first consider the operation of a video system in accordance with the prior art. FIG. 5 indicates the appearance of a circular object 140 viewed by a borescope having therein optics 142, which are constructed in accordance with the prior art, the borescope also including a 525 line formatted CCD imager 120. The image projected on imager 120 occupies up to 488 horizontal lines. As discussed above, the CCD output is coupled to video electronics and thence directed to a display monitor, indicated schematically by arrows 125, 125'. On the left side of FIG. 5 the monitor display 127 represents the output of a 525 line video monitor, with 488 scan lines being presented to the viewer. The image 148 thus occupies the full vertical dimension 146 of the monitor display 127, and is an undistorted representation of the object 140.

The right side of FIG. 5 shows the result when the output from CCD imager 120 is ultimately displayed on a 625 line monitor 127'. Image 148' now occupies 488 of the 588 available lines, shown as dimension 147. The top and bottom areas 149, 149 of monitor display 127' contain no video information relating to object 140. The vertical dimension of image 148' is compressed by a factor of 488/588, while the horizontal dimension remains undistorted.

Returning now to FIGS. 1 and 2 a negative cylindrical compensating lens 29 having a horizontal axis is interposed between the last objective lens 19 and the light receptive areas of imager 20. Principal rays 23, 23 extend from the vertical margins of the field of view through the optics, and are incident on the CCD surface at points outside the optically active area of the CCD (indicated by dimension 21 in FIG. 2). The CCD as disposed in the preferred embodiment has an active area approximating 3.3×4.4 mm in horizontal and vertical dimensions respectively. In the absence of cylindrical lens 29, principal rays 23, 23 would follow the courses indicated by lines 23', 23' and would precisely subtend dimension 21 on the CCD. It will be evident that optical information lying outside lines 23', 23' will not be displayed by monitor 26, and that the displayed image will be truncated. The cylindrical compensation produced by lens 29 produces a vertical elongation of the image projected on the CCD that is exactly opposite in magnitude to the vertical compressive effect caused by a 588 line PAL monitor interfaced to video electronics that expect a 488 line display.

The effect of introducing cylindrical lens 29 into the optical assembly can be more clearly understood with reference to FIG. 6. The system shown is similar to that of FIG. 5, except now a compensating cylindrical lens 129 having a horizontal cylindrical axis has been introduced in the optical path leading from the object 140 to the NTSC CCD 120. When the CCD output is ultimately displayed on the NTSC monitor display 127 the image 248 is vertically elongated and its vertical extremes truncated. Directing the CCD output to PAL monitor display 127' again results in dark areas 149, 149. The image 248' remains vertically truncated, however it otherwise is undistorted.

The system described above has been successfully operated in prototype in an endoscope, using a compensating cylindrical lens constructed in accordance with the specifications given in Table 1, which refers to dimensions illustrated in FIGS. 3 and 4.

TABLE 1

| Material | LaSF-9 |
|---|---|
| Optical Coating | MgF2 optimized for 520 nm (one surface only) |
| Radius Tolerance | 5 Rings power 1 Ring irregularity |
| Optical Centering with mechanical axis | 0.5 mm. |
| Radial dimension 35 | 0.197 in. |
| Dimension 36 | 0.310 in. |
| Dimension 37 | 0.146 in. |
| Dimension 38 | 0.258 in. |

Figure 7:
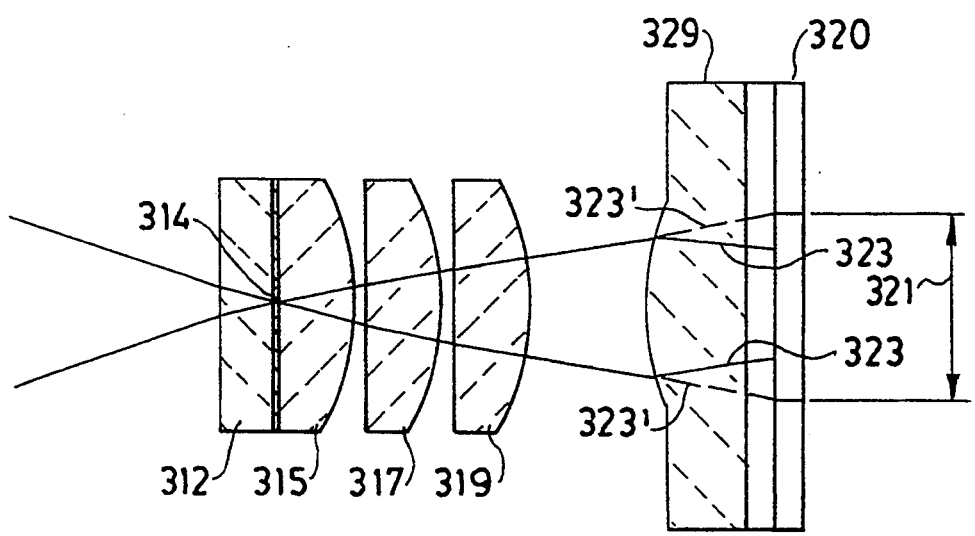
FIG. 7 is a top view of an optical arrangement in accordance with an alternate embodiment of the invention.

Turning now to FIG. 7, there is shown an optical arrangement in accordance with an alternate embodiment of the invention. The general structure is similar to that described in the first embodiment with reference to FIG. 2. However the lens 329 now has a positive cylinder with a vertical axis. Referring back to FIG. 2, it will be evident that the power of lens 329 is opposite that of lens 29, and that the axis of lens 329 is orthogonal to the axis of lens 29. The dotted lines 323', 323' indicate the light path that would be taken by principal rays, shown as solid lines 323, 323 in the absence of lens 329. The lines 323', 323' also delineate the horizontal extent of the optically active area of NTSC CCD 320, shown as dimension 321 in FIG. 7. It will be evident the horizontal dimension of an object being viewed will be minified. On a PAL display the vertical extremes of the image will be fully visualized, and the horizontal dimension will be reduced. The cylindrical power of lens 329 is adjusted to produce an undistorted image in the PAL monitor.

While this invention has been explained with reference to the structure disclosed herein, it is not confined to the details set forth and this application is intended to cover any modifications and changes as may come within the scope of the following claims:

What is claimed is:
1. A video system comprising:
    photodetector means for sensing a pattern of light incident thereon, said pattern being a first representation of a visual field of interest, said photodetector means having an output in accordance with a first video convention;
    video electronic means coupled to said output of said photodetector means for producing a video signal in accordance with a second video convention;
    video output means adapted to said second video convention and accepting said video signal for producing a second representation of said field of interest;
    compensating optical means disposed in an optical path extending from said photodetector means to said field of interest for varying at least one dimension of said pattern;
    whereby said compensating optical means corrects a systematic distortion of said second representation which results from an incompatibility between said first video convention and said second video convention.

2. The system in accordance with claim 1, wherein said compensating optical means comprises a cylindrical lens.

3. The system in accordance with claim 2 wherein said cylindrical lens has a horizontal axis and a concave face directed toward said field of interest for magnifying a vertical dimension of said pattern.

4. The system in accordance with claim 2, wherein said cylindrical lens has a vertical axis and a convex face directed toward said field of interest for minifying a horizontal dimension of said pattern.

5. The system in accordance with claim 1, wherein said first video convention is 525 horizontal lines and said second video convention is 625 horizontal lines, and said photodetector means comprises a CCD having a format comprising about 510 pixels per horizontal line and about 488 horizontal lines.

6. A video probe, comprising:
an optical assembly disposed at a distal end of an insertion tube;
an optical sensor having a pixel format in accordance with a first video convention for sensing an optical pattern projected thereon by said optical assembly, said optical pattern being representative of a field of interest;
video electronic means adapted to said pixel format and connected to said optical sensor for producing an output in accordance with a second video convention;
a monitor adapted to said second video convention and connected to said video electronic means for displaying said output, said monitor producing a first distortion of said representation of said optical pattern in accordance with an incompatibility between said first video convention and said second video convention; and
compensating optical means disposed in an optical path extending from said field of interest to said optical sensor for producing a second distortion of said projected optical pattern;
whereby said compensating means corrects said first distortion.

7. The video probe in accordance with claim 6, wherein said compensating optical means comprises a cylindrical lens.

8. The video probe in accordance with claim 7 wherein said cylindrical lens has a horizontal axis and a concave face directed toward said field of interest for magnifying a vertical dimension of said optical pattern.

9. The video probe in accordance with claim 7, wherein said cylindrical lens has a vertical axis and a convex face directed toward said field of interest for minifying a horizontal dimension of said optical pattern.

10. The video probe in accordance with claim 6, wherein said first video convention is 525 horizontal lines and said second video convention is 625 horizontal lines, and said photodetector means comprises a CCD having a format comprising about 510 pixels per horizontal line and about 488 horizontal lines.

11. A video probe, comprising:
an optical assembly disposed at a distal end of an insertion tube;
an CCD optical sensor having a format comprising about 510 pixels per horizontal line and about 488 horizontal lines for sensing an optical pattern projected thereon by said optical assembly, said optical pattern being representative of a field of interest;
video electronic means adapted to said format and connected to said optical sensor for producing an output in accordance with a 625 horizontal line video convention;
a monitor adapted to the 625 horizontal line video convention and connected to said video electronic means for displaying said output, said monitor producing a first distortion of said output; and
a cylindrical lens disposed in an optical path extending from said field of interest to said optical sensor for producing a second distortion of said projected optical pattern;
whereby said compensating means corrects said first distortion and said monitor produces an undistorted display of said field of interest.

12. The video probe in accordance with claim 11 wherein said cylindrical lens has a horizontal axis and a concave face directed toward said field of interest for magnifying a vertical dimension of said optical pattern.

13. The video probe in accordance with claim 12, wherein said cylindrical lens has a vertical axis and a convex face directed toward said field of interest for minifying a horizontal dimension of said optical pattern.

* * * * *